(12) United States Patent
Liu et al.

(10) Patent No.: US 11,548,862 B2
(45) Date of Patent: Jan. 10, 2023

(54) PREPARATION METHOD OF SELENIUM-CONTAINING HETEROCYCLIC COMPOUNDS

(71) Applicant: Wenzhou University, Wenzhou (CN)

(72) Inventors: Miaochang Liu, Wenzhou (CN); Liguo Lu, Wenzhou (CN); Chuanli Chen, Wenzhou (CN); Yunbing Zhou, Wenzhou (CN); Huayue Wu, Wenzhou (CN)

(73) Assignee: WENZHOU UNIVERSITY, Wenzhou (CN)

( * ) Notice: Subject to any disclaimer, the term of this patent is extended or adjusted under 35 U.S.C. 154(b) by 0 days.

(21) Appl. No.: 17/527,544

(22) Filed: Nov. 16, 2021

(65) Prior Publication Data
US 2022/0169623 A1    Jun. 2, 2022

(30) Foreign Application Priority Data
Nov. 27, 2020    (CN) .......................... 202011360011.2

(51) Int. Cl.
| | | |
|---|---|---|
| C07D 293/06 | (2006.01) | |
| C07D 293/02 | (2006.01) | |
| C07D 293/08 | (2006.01) | |
| C07D 293/10 | (2006.01) | |

(52) U.S. Cl.
CPC .......... *C07D 293/06* (2013.01); *C07D 293/02* (2013.01); *C07D 293/08* (2013.01); *C07D 293/10* (2013.01)

(58) Field of Classification Search
CPC .................................................. C07D 293/06
See application file for complete search history.

(56) References Cited

PUBLICATIONS

V P Litvinov et al., "Selenium-containing heterocycles", Russian Chemical Reviews, 1997, pp. 923-951, vol. 66, No. 11.
Masayuki Ninomiya et al., "Biologically significant selenium-containing heterocycles", Coordination Chemistry Reviews, 2011, pp. 2968-2990, vol. 255.
Mohamed Elsherbini et al., "Recent advances in the chemistry of selenium-containing heterocycles: Six-membered ring systems", Coordination Chemistry Reviews, 2017, pp. 110-126, vol. 330.
Young-Joon Park et al., "1,3-Selenazol-4-one Derivatives Inhibit Inducible Nitric Oxide-Mediated Nitric Oxide Production in Lipopolysaccharide-Induced BV-2 Cells", Biol. Pharm. Bull., 2003, pp. 1657-1660,vol. 26, No. 12.
Kaname Tsuchii et al., "Highly Selective Sequential Addition and Cyclization Reactions Involving Diphenyl Diselenide, an Alkyne, and Alkenes under Visible-Light Irradiation", Angew. Chem. Int. Ed., 2003, pp. 3490-3493, vol. 42.
Veronica De Silva et al., "Selenium Redox Cycling in the Protective Effects of Organoselenides against Oxidant-Induced DNA Damage", J. Am. Chem. Soc., 2004, pp. 2409-2413, vol. 126, No. 8.
Philip R. Taylor et al., "Science Peels the Onion of Selenium Effects on Prostate Carcinogenesis", Journal of the National Cancer Institute, May 5, 2004, pp. 645-647, vol. 96, No. 9.

*Primary Examiner* — Paul V Ward
(74) *Attorney, Agent, or Firm* — WPAT, PC

(57) ABSTRACT

A reaction of azacyclopropane derivative with elemental selenium and TMSCN to construct a selenium-containing heterocycle under metal-free and additive-free conditions is provided. The new strategy features no metal participation, no additive promotion, a wide substrate selection range and a good functional group compatibility, and provides an efficient and green approach to constructing a variety of selenium-containing heterocyclic compounds in a highly concise way.

10 Claims, No Drawings

PREPARATION METHOD OF SELENIUM-CONTAINING HETEROCYCLIC COMPOUNDS

FIELD OF THE DISCLOSURE

The disclosure relates to the field of preparation technologies of selenium-containing heterocyclic compounds, and more particularly to a preparation method of a selenium-containing heterocyclic compound.

BACKGROUND OF THE DISCLOSURE

Selenium-containing heterocyclic derivatives have great application value (see V P Litvinov et al., "Selenium-containing heterocycles", Russian Chemical Reviews, 1997, pp. 923-951, vol. 66, No. 11; Masayuki Ninomiya et al., "Biologically significant selenium-containing heterocycles", Coordination Chemistry Reviews, 2011, pp. 2968-2990, vol. 255; Mohamed Elsherbini et al., "Recent advances in the chemistry of selenium-containing heterocycles: Six-membered ring systems", Coordination Chemistry Reviews, 2017, pp. 110-126, vol. 330). These compounds can be used as a very useful pharmaceutical activity intermediate in synthesis of a series of selenium-containing heterocycles and other products with great application value (see Young-Joon PARK et al., "1,3-Selenazol-4-one Derivatives Inhibit Inducible Nitric Oxide-Mediated Nitric Oxide Production in Lipopolysaccharide-Induced BV-2 Cells", Biol. Pharm. Bull., 2003, pp. 1657-1660, vol. 26, No. 12; Kaname Tsuchii et al., "Highly Selective Sequential Addition and Cyclization Reactions Involving Diphenyl Diselenide, an Alkyne, and Alkenes under Visible-Light Irradiation", Angew. Chem. Int. Ed., 2003, pp. 3490-3493, vol. 42). The selenium-containing heterocycles become privileged structural scaffolds due to their interesting biological and medical properties (see Veronica De Silva et al., "Selenium Redox Cycling in the Protective Effects of Organoselenides against Oxidant-Induced DNA Damage", J. AM. CHEM. SOC., 2004, pp. 2409-2413, vol. 126, No. 8; Philip R. Taylor et al., "Science Peels the Onion of Selenium Effects on Prostate Carcinogenesis", Journal of the National Cancer Institute, May 5, 2004, pp. 645-647, vol. 96, No. 9). For example, they are used as inducible nitric oxide synthase (iNOS) inhibitor. After referring to the previous work/study and our research group's similar in-depth research on the efficient insertion of elemental selenium, we envisage that the three-component ring-opening reaction of azacyclopropane derivatives, elemental selenium and TMSCN provides a series of selenium-containing heterocycles in good yields under mild conditions. Finally, a convenient, feasible, easy-to-operate, high-yield, environmentally-friendly and efficient method for constructing such selenium-containing heterocyclic molecules in one step is obtained.

SUMMARY OF THE DISCLOSURE

An objective of the disclosure is to provide a new method for preparing a selenium-containing heterocyclic compound. The method uses azacyclopropane derivative, elemental selenium and trimethylsilyl cyanide (TMSCN) to obtain five to seven-membered selenium-containing heterocyclic compounds by ring-opening reaction under mild conditions. The method has advantages of features convenience, feasibility, easy operation, high yield, environmental friendliness, and broad functional group compatibility.

Specifically, the disclosure provides an efficient method for the synthesis of a selenium-containing heterocyclic compound, including the following steps:

sequentially adding azacyclopropane derivative of formula I, selenium powder, trimethylsilyl cyanide (TMSCN) and an organic solvent to a reactor equipped with a magnetic stirrer, subsequently replacing atmosphere in the reactor with an inert atmosphere, heating and stirring to obtain a reaction mixture, diluting the reaction mixture with ethyl acetate after the reaction, and then filtering the diluted reaction mixture through a silica gel pad to obtain a filtrate, concentrating the filtrate under a reduced pressure to obtain a residue, and then purifying the residue by silica gel flash chromatography, thereby obtaining a selenium-containing heterocyclic compound of formula II. A formula for the reaction is as follows:

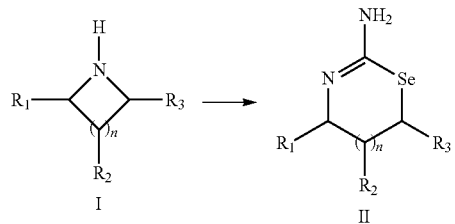

where n=0, 1, or 2.

where $R_1$, $R_2$ and $R_3$ represent substituent groups on a connected ring, which are independently selected from the groups consisting of hydrogen group, $C_{1-20}$ alkyl group, $C_{6-20}$ aryl group, $C_{3-20}$ cycloalkyl group and $C_{6-20}$ aryl-group-$C_{1-20}$ alkyl-group; or adjacent two of which being $R_1/R_2$, $R_2/R_2$, $R_2/R_3$ or $R_1/R_3$ substituent groups are connected to each other and form one of saturated or unsaturated five to seven membered carbon rings together with carbon atoms connecting the adjacent two substituent groups.

In an embodiment of the disclosure, when n=0, $R_1$ is one selected from the groups consisting of the $C_{1-20}$ alkyl group and the $C_{6-20}$ aryl-group-$C_{1-20}$ alkyl-group, and $R_3$ is the hydrogen group.

When n=1, $R_1$, $R_2$ and $R_3$ each are the hydrogen group.

When n=2, $R_1$, $R_2$, $R_3$ each are the hydrogen group, or adjacent two of being $R_1/R_2$, $R_2/R_2$ or $R_2/R_3$ substituent groups are connected to each other and form the one of saturated or unsaturated five to seven membered carbon rings together with the carbon atoms connecting the adjacent two substituent groups.

In an embodiment of the disclosure, the $C_{1-20}$ alkyl group can be selected from the groups consisting of methyl group, ethyl group, n-propyl group, isopropyl group, n-butyl group, isobutyl group, tert butyl group, n-amyl group, isopentyl group, neopentyl group, n-hexyl group, n-heptyl group, n-octyl group, n-nonyl group and n-decyl group. The $C_{6-20}$ aryl group can be selected from the groups consisting of phenyl group, naphthyl group, anthracyl group and phenanthryl group. The $C_{3-20}$ cycloalkyl group can be selected from the groups consisting of cyclopropyl group, cyclobutyl group, cyclopentyl group, cyclohexyl group and cycloheptyl group. The one of saturated or unsaturated five to seven membered carbon rings is selected from the group consisting of cyclopentane ring, cyclohexane ring, benzene ring and naphthalene ring.

In an embodiment of the disclosure, when n=0, $R_1$ is one of n-hexyl group and benzyl group, and $R_3$ is the hydrogen group.

When n=1, $R_1$, $R_2$ and $R_3$ each are the hydrogen group.

When n=2, $R_1$, $R_2$ and $R_3$ each are the hydrogen group, or adjacent two $R_1/R_2$ substituent groups are connected to each other and form a benzene ring structure together with carbon atoms connecting the adjacent two $R_1/R_2$ substituent groups, and the other $R_2/R_3$ substituent groups each are the hydrogen group.

In an embodiment of the disclosure, the organic solvent is one selected from alcoholic solvents. Specifically, the organic solvent is one selected from the group consisting of methanol, ethanol and isopropanol, and more specifically isopropanol.

In an embodiment of the disclosure, reaction temperature of the heating and stirring for reaction is 80~120° C. Specifically, the reaction temperature is 100° C. Reaction time of the heating and stirring for reaction is 4~48 h. Specifically, the reaction time is 12~24 h, and more specifically 24 h.

In an embodiment of the disclosure, a molar ratio of the azacyclopropane derivative of the formula I, the selenium powder and the TMSCN is 1:(2~5):(1~3). Specifically, the molar ratio of the azacyclopropane derivative of the formula I, the selenium powder and the TMSCN is 1:3:2.

In an embodiment of the disclosure, the inert atmosphere is one of nitrogen atmosphere and argon atmosphere. Specifically, the inert atmosphere is nitrogen atmosphere.

Compared with the prior art, the embodiments of the disclosure may mainly have the following beneficial effects.

The disclosure first discloses a synthetic strategy of five to seven membered selenium-containing heterocyclic compounds by ring opening reaction under mild conditions by using the azacyclopropane derivatives, elemental selenium and the TMSCN. The new strategy has many advantages including metal-free participation, additive-free promotion, a wide substrate selection range and a good functional group compatibility, and provides an efficient and green approach to synthesizing a variety of selenium-containing heterocyclic compounds in a highly concise way.

DETAILED DESCRIPTION OF EMBODIMENTS

The disclosure is further described below in combination with specific embodiments. In the illustrated embodiments, unless otherwise specified, the methods adopted are conventional methods in the related art, and the reagents used can be purchased through conventional commercial channels and/or prepared through known organic synthesis methods.

Embodiments 1-14

Using 2-hexylazacyclopropane as a template substrate, optimal reaction conditions are selected (see Table 1).

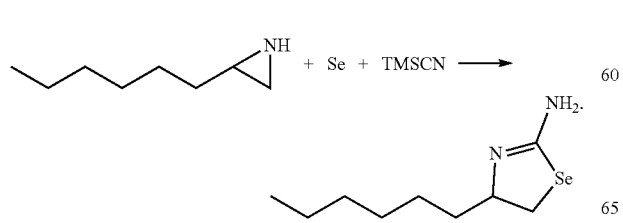

TABLE 1

| Embodiment[a] | Solvent | Reaction temperature | Yield (%)[b] |
|---|---|---|---|
| 1 | Dimethyl sulfoxide (DMSO) | 90 | NR |
| 2 | toluene | 90 | NR |
| 3 | Dioxane | 90 | NR |
| 4 | N-Methyl pyrrolidone (NMP) | 90 | NR |
| 5 | acetonitrile | 90 | NR |
| 6 | Dichloroethane (DCE) | 90 | 25 |
| 7 | Tetrahydrofuran (THF) | 90 | 39 |
| 8 | Isopropanol (IPA) | 90 | 78 |
| 9 | Ethanol (EtOH) | 90 | 74 |
| 10 | IPA | 25 | NR |
| 11 | IPA | 60 | 34 |
| 12 | IPA | 80 | 66 |
| 13 | IPA | 100 | 94 |
| 14 | IPA | 120 | 87 |

Where, in table 1, [a] represents using the 2-hexylazacyclopropane (0.5 millimole (mmol)), selenium powder (1.5 mmol), trimethylsilyl cyanide (TMSCN) (1.0 mmol) to react in solvent (2 milliliters (mL)) at T ° C. and $N_2$ for 24 hours (h); [b] represents the yield of products separated by a column chromatography.

Taking the embodiment 13 as an example, typical reaction operations are as follows:

the 2-hexylazacyclopropane (0.5 mmol), the selenium powder (3.0 equiv), the TMSCN (2.0 equivalents (equiv)) and isopropanol (2 mL) are added into a 10 mL pressure tube equipped with a stirring magnet (also referred to as a magnetic stirrer) to obtain a reaction mixture. The reaction mixture is stirred under nitrogen protection at 100° C. for 24 h. After the reaction, the reaction mixture is diluted with 10 mL of ethyl acetate, filtered through a silica gel pad and concentrated under a reduced pressure to obtain a residue. Then the residue is purified by silica gel flash chromatography to obtain a pure target product. Yellow liquid (110 milligrams (mg), 94% yield), $CH_3OH$/dichloromethane (DCM)=1/10. $^1$H nuclear magnetic resonance (NMR) (400 MHz, $CDCl_3$): δ 6.54 (s, 2H), 4.22-4.17 (m, 1H), 3.64 (dd, J=8.0, 5.6 Hz, 1H), 3.27 (dd, J=8.0, 6.0 Hz, 1H), 1.82-1.76 (m, 1H), 1.66-1.59 (m, 1H), 1.33-1.24 (m, 8H), 0.84 (t, J=5.2 Hz, 3H); $^{13}$C NMR (125 MHz, deuterated chloroform ($CDCl_3$)): δ 169.6, 65.0, 34.2, 32.8, 31.6, 29.0, 26.1, 22.6, 14.1.

The experimental results in Table 1 show that the template reaction shows different reactivity in various solvents. In polar proton solvents, the yield of template reaction is generally high, especially in the case of isopropanol as solvent, the target product is obtained in 94% yield without any additives. Finally, considering factors of economy and efficiency, the isopropanol is selected as the reaction solvent and reacted at 100° C. for 24 hours under the protection of nitrogen.

Embodiment 15

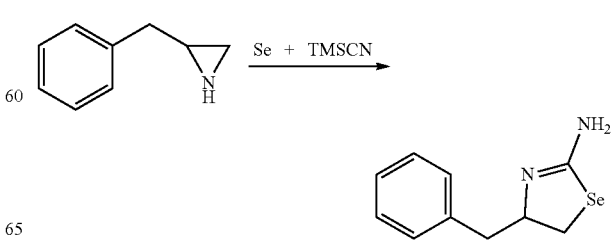

2-benzylazacyclopropane (0.5 mmol), selenium powder (3.0 equiv), TMSCN (2.0 equiv) and isopropanol (2 mL) are added into a 10 mL pressure tube equipped with a stirring magnet to obtain a reaction mixture. The reaction mixture is stirred under nitrogen protection at 100° C. for 24 h. After the reaction, the reaction mixture is diluted with 10 mL of ethyl acetate, filtered through a silica gel pad and concentrated under a reduced pressure to obtain a residue. Then the residue is purified by silica gel flash chromatography to obtain a pure target product. Yellow liquid (64.8 mg, yield 54%), $CH_3OH/DCM=1/10$. $^1H$ NMR (400 MHz, $CDCl_3$): δ 7.32-7.28 (m, 2H), 7.24-7.20 (m, 3H), 5.64 (s, 2H), 4.38-4.33 (m, 1H), 3.46-3.40 (m, 1H), 3.28-3.21 (m, 1H), 3.08-3.01 (m, 1H), 2.81-2.75 (m, 1H); $^{13}C$ NMR (125 MHz, $CDCl_3$): δ 158.7, 138.6, 129.2, 128.6, 126.5, 73.3, 41.1, 36.4.

Embodiment 16

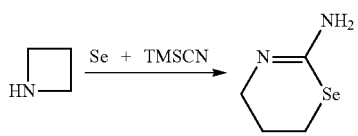

Azacyclobutane (0.5 mmol), selenium powder (3.0 equiv), TMSCN (2.0 equiv) and isopropanol (2 mL) are added into a 10 mL pressure tube equipped with a stirring magnet to obtain a reaction mixture. The reaction mixture is stirred under nitrogen protection at 100° C. for 24 h. After the reaction, the reaction mixture is diluted with 10 mL of ethyl acetate, filtered through a silica gel pad and concentrated under a reduced pressure to obtain a residue. Then the residue is purified by silica gel flash chromatography to obtain a pure target product. Yellow liquid (46 mg, yield 56%), $CH_3OH/DCM=1/10$. $^1H$ NMR (400 MHz, hexadeuteroacetone ($CD_3COCD_3$)): δ 3.68-3.64 (m, 2H), 3.46-3.42 (m, 2H), 2.34-2.30 (m, 2H), 2.12 (s, 2H); $^{13}C$ NMR (125 MHz, $CD_3COCD_3$): δ 166.9, 43.9, 23.3, 23.2.

Embodiment 17

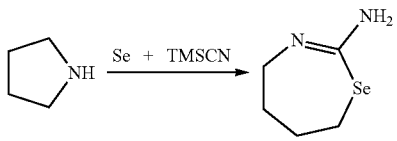

Tetrahydropyrrole (0.5 mmol), selenium powder (3.0 equiv), TMSCN (2.0 equiv) and isopropanol (2 mL) are added into a 10 mL pressure tube equipped with a stirring magnet to obtain a reaction mixture. The reaction mixture is stirred under nitrogen protection at 100° C. for 24 h. After the reaction, the reaction mixture is diluted with 10 mL of ethyl acetate, filtered through a silica gel pad and concentrated under a reduced pressure to obtain a residue. Then the residue is purified by silica gel flash chromatography to obtain a pure target product. Colorless liquid (71 mg, yield 80%), $CH_3OH/DCM=1/10$. $^1H$ NMR (400 MHz, $CD_3COCD_3$): δ 4.18-4.15 (m, 4H), 2.26-2.23 (m, 4H), 2.09 (s, 2H); $^{13}C$ NMR (125 MHz, $CD_3COCD_3$): δ 186.5, 55.5, 46.3, 25.5, 24.9.

Embodiment 18

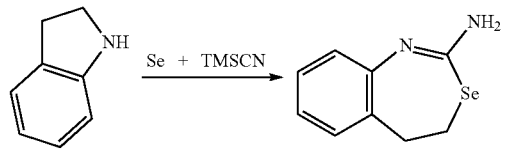

Dihydroindole (0.5 mmol), selenium powder (3.0 equiv), TMSCN (2.0 equiv) and isopropanol (2 mL) are added into a 10 mL pressure tube equipped with stirring magnet to obtain a reaction mixture. The reaction mixture is stirred under nitrogen protection at 100° C. for 24 h. After the reaction, the reaction mixture is diluted with 10 mL of ethyl acetate, filtered through a silica gel pad and concentrated under a reduced pressure to obtain a residue. Then the residue is purified by silica gel flash chromatography to obtain a pure target product. Yellow liquid (39 mg, yield 34%), $CH_3OH/DCM=1/10$. $^1H$ NMR (400 MHz, DMSO): δ 8.91 (s, 1H), 8.22 (s, 2H), 7.25-7.23 (m, 1H), 7.18-7.13 (m, 1H), 7.05-7.00 (m, 1H), 4.12-4.07 (m, 2H), 3.09-3.05 (m, 2H); $^{13}C$ NMR (125 MHz, DMSO): δ 174.0, 143.0, 134.0, 125.8, 125.0, 123.5, 116.7, 53.1, 26.2.

The above illustrated embodiments are only preferred embodiments determined by the inventor after a large number of tests and screening, and are not an exhaustive list of feasible embodiments of the disclosure. For those skilled in the art, any obvious changes made to the synthetic route of the disclosure without departing from the synthetic route of the disclosure shall be considered to be included in the protection scope of the claims of the disclosure.

What is claimed is:

1. A preparation method of a selenium-containing heterocyclic compound, comprising the following steps:
   sequentially adding azacyclopropane derivative of formula I, selenium powder, trimethylsilyl cyanide (TMSCN) and an organic solvent to a reactor equipped with a magnetic stirrer,
   subsequently replacing atmosphere in the reactor with an inert atmosphere, heating and stirring for reaction to obtain a reaction mixture,
   diluting the reaction mixture with ethyl acetate after the reaction, and then filtering through a silica gel pad to obtain a filtrate,
   concentrating the filtrate under a reduced pressure to obtain a residue, and then purifying the residue by silica flash chromatography, thereby obtaining a selenium-containing heterocyclic compound of formula II;
   wherein a formula for the reaction is as follows:

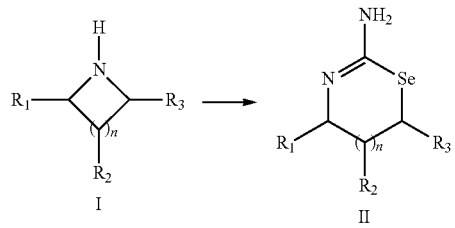

where n=2;
where adjacent two $R_1/R_2$ substituent groups are connected to each other and form a benzene ring structure together with carbon atoms connecting the adjacent two $R_1/R_2$ substituent groups, and adjacent two $R_2/R_3$ substituent groups each are hydrogen group;

wherein the organic solvent is one selected from alcoholic solvents.

2. The preparation method according to claim 1, wherein the organic solvent is one selected from the group consisting of methanol, ethanol and isopropanol.

3. The preparation method according to claim 1, wherein the organic solvent is isopropanol.

4. The preparation method according to claim 1, wherein reaction temperature of the heating and stirring for reaction is 80~120° C., reaction time of the heating and stirring for reaction is 4~48 hours (h).

5. The preparation method according to claim 4, wherein the reaction temperature is 100° C., and the reaction time is 12~24 h.

6. The preparation method according to claim 5, wherein the reaction time is 24 h.

7. The preparation method according to claim 1, wherein a molar ratio of the azacyclopropane derivative of the formula I, the selenium powder and the TMSCN is 1:(2~5):(1~3).

8. The preparation method according to claim 7, wherein the molar ratio of the azacyclopropane derivative of the formula I, the selenium powder and the TMSCN is 1:3:2.

9. The preparation method according to claim 1, wherein the inert atmosphere is one of nitrogen atmosphere and argon atmosphere.

10. The preparation method according to claim 1, wherein the inert atmosphere is argon atmosphere.

* * * * *